(12) United States Patent
Yeh (10) Patent No.: US 7,803,396 B2
(45) Date of Patent: Sep. 28, 2010

(54) PRODUCT FOR CONTROLLING DISSOLVING RATE OF ORTHOPEDIC IMPLANT MATERIAL AND PROCESS OF PRODUCING THE SAME

(75) Inventor: Chin-Chi Yeh, Kaohsiung (TW)

(73) Assignee: Nan-Hui Yeh, Kaohsiung (TW)

( * ) Notice: Subject to any disclaimer, the term of this patent is extended or adjusted under 35 U.S.C. 154(b) by 872 days.

(21) Appl. No.: 11/581,429

(22) Filed: Oct. 17, 2006

(65) Prior Publication Data

US 2007/0087030 A1    Apr. 19, 2007

(51) Int. Cl.
*A61F 2/00* (2006.01)
*A61F 2/28* (2006.01)
*A61K 33/42* (2006.01)
*A61L 27/32* (2006.01)
*C01B 25/26* (2006.01)
*C01F 11/46* (2006.01)

(52) U.S. Cl. .................... 424/426; 424/602; 623/16.11; 427/2.27; 423/308; 423/555

(58) Field of Classification Search ........................ None
See application file for complete search history.

(56) References Cited

U.S. PATENT DOCUMENTS 5,424,471 A * 6/1995 Kennedy et al. ............ 558/146
6,497,901 B1 * 12/2002 Royer ......................... 424/468

OTHER PUBLICATIONS

Rodenas et al, 2005. Surface properties of various powdered hyxroxyapatites. Journal of Colloid and Interface Science, vol. 290:145-154.*

* cited by examiner

*Primary Examiner*—Jean C. Witz
*Assistant Examiner*—Raymond P Yeager
(74) *Attorney, Agent, or Firm*—Rosenberg, Klein & Lee (57) ABSTRACT

A product controlling dissolving rate of biomedical orthopedic implant material and a process of manufacturing the same are disclosed. At constant temperature and humidity and under vacuum, treatment solution is forced to diffuse to the material to form a second phase as a means of controlling the dissolving rate. Different treatment solution can form the phases having different structures from that of matrix. The inventive product has a structure of laminate concentric circle. The second phase and the structure of laminate concentric circle are used as ways for medicine release.

17 Claims, 13 Drawing Sheets

(3 of 13 Drawing Sheet(s) Filed in Color)

PRODUCT FOR CONTROLLING DISSOLVING RATE OF ORTHOPEDIC IMPLANT MATERIAL AND PROCESS OF PRODUCING THE SAME

BACKGROUND OF THE INVENTION

1. Field of the Invention

The invention generally relates to a product for controlling dissolving rate of orthopedic implant material and a manufacture process that diffuses a treatment solution into biomedical orthopedic implant material to form a second phase on the implant material at constant temperature and humidity.

2. Description of the Related Art

Bone aging and osteoporosis are common cases in clinics of orthopedics. Bone substitutes are increasingly in urgent need as the population of old ages increases, bone substitutes. Bone damages caused by disease or trauma can be recovered by partially filling up bone filling material. The bone filling material includes autograft material, allrgraft material and processed animal bone. Among those, orthopedic implant cement based calcium sulfate, such as Collagrant and OSTEOSET Bone Graft susbstutites, has been used commonly. However, it has some disadvantages such as non-availability, self-repelling, infection, need of second surgery, too fast dissolving rate, growth of soft fiber tissues. In addition, complicate human bone structure and stress generated accordingly when bone recovery proceeds limit the application of those bone substitutes in use. Therefore, how to avoid the need of second surgery, lowering loss rate of implant material as substitutes and promote growth of bone cells are key issues to study in the field. Keeping the loss rate of bone filling material as close to the bone growth rate helps avoid the presence of fiber tissues. Bone filling material is an implant material, including single material or composite, which promotes the bone recovery in osteogenic, osteoinductive or osteoconductive ways. The bone filling material is divided into three main categories of autograft, allrgraft, xenograft and synthetic materials and blends thereof, according to its functional construction. The synthetic material includes osteoconductive blocks or granules, osteoconductive cement, osteoinductive proteins and composites.

The appearance of synthetic materials broadens the application of the bone filling material. The synthetic material can be also classified into two main categories: ceramics and polymers. The ceramic synthetic material is mainly based on either calcium phosphate or calcium sulfate, both of which have good bio-compatibility and are absorbable in vivo. Examples of the polymeric synthetic material are PMMA which cannot be absorbed in vivo, and PLLA which can be absorbed in vivo. Calcium sulfate, so-called gypsum, includes calcium sulfate anhydrate (CaSO4), calcium sulfate hemihydrate (CaSO4.½H2O) and calcium sulfate dihydrate (CaSO4.2H2O). High-hardness gypsum most commonly used for medical purpose is calcium sulfate hemihydrate which generate crystalline water and turns into calcium sulfate dihydrate to offer solidification after meets water. The chemical scheme is as follows:

$CaSO_4 \cdot \frac{1}{2}H_2O + \frac{3}{2}H_2O \longrightarrow CaSO_4 \cdot 2H_2O$ During the reaction, more water, in addition to what is needed for solification, is needed for stirring thoroughly reactants. The more water adds into, the much time of solification needs. After the reaction completes, excess of water still remained inside the structure of calcium sulfate distills into vapors and voids form accordingly. Therefore, the more water adds in, the weaker of the structural strength of calcium sulfate becomes. Calcium sulfate hemihydrate is obtained by dehydrating calcium sulfate dihydrate by heat. Calcium sulfate hemihydrate with inherent humidity-absorbance can be used to control the crystallization of calcium sulfate dihydrate reduced from calcium sulfate hemihydrate to get stronger products. Calcium sulfate hemihydrate can be divided into a, (3 types of hemi-calcium sulfates according to its physical properties.

The inventors have intensively studied on controlling loss rate of the bone filling material as close to growth rate of bone using calcium sulfate, while avoiding the need of second surgery, avoiding the growth of promoting the growth of osteocells.

SUMMARY OF THE INVENTION

The inventors have developed one technology that can control dissolving rate of bio-medical orthopedic implant material at constant temperature and humidity. In the invention, different kinds of treatment liquids are used to form on the implant material under vacuum second phases that have structures different from that of matrix. The second phase can be used to control the dissolving rate of the bio-medical implant material. It is noted that the second phase thus formed is in the shape of laminate concentric circle, and has dense and uniformly distributed configuration.

One object of the invention is to provide a process of controlling dissolving rate of bio-medical orthopedic implant material to make loss rate of bone filling material close to bone growth rate while avoid the growth of fiber tissues.

Another object of the invention is to provide a second phase grown on surfaces of bio-medical implant material. The second phase has a structure different from that of a matrix. At constant temperature and constant humidity, the second phase having structure different from that of the matrix is formed on the bio-medical implant material by using different treatment liquids under vacuum. In this way, the loss rate of bone filling rate can be well controlled.

Still, another object of the invention is to provide a structure of laminate concentric circle that controls the dissolving rate of a bio-medical implant material. The structure of laminate concentric circle has a dense and uniformly distributed configuration, which can be easily stored and applied, and made at low cost and with high quality.

Furthermore, another object of the invention is to provide a process of providing surfaces of bio-medical implant material as one way for drug release, which can be applied to similar materials.

Calcium sulfate dihydrate is dehydrated by heat and then turns into calcium sulfate hemihydrate, and vice-versa. Stronger structure with longer dissolving time can be obtained by controlling the crystallinity of calcium sulfate dihydrate reduced from calcium sulfate hemihydrate. To achieve a better control of the crystallinity of calcium sulfate dihydrate reduced from calcium sulfate hemihydrate, it needs a constant temperature and humidity environment, by using a constant temperature/humidity chamber for example, to adjust three main variables of temperature, humidity and time in controlling amount of hemi-calcium sulfate turned into calcium sulfate dihydrate. On the other hand, experimental data about dissolving rates is used for comparison.

Calcium sulfate, so-called gypsum, includes calcium sulfate anhydrate (CaSO4), calcium sulfate hemihydrate (CaSO4.½H2O) and calcium sulfate dihydrate (CaSO4.2H2O). High-hardness gypsum most commonly used for medical purpose is calcium sulfate hemihydrate which generates crystalline water and turns into calcium sulfate dihydrate to offer solidification after contacts with water. The chemical scheme is as follows:

During the reaction, more water, in addition to what is needed for solidification, is needed for stirring reactants thoroughly. The more water adds into, the much time of solidification needs. After the reaction completes, excess of water still remained inside the structure of calcium sulfate distills into vapors and voids form accordingly. Therefore, the more water adds in, the weaker of the structural strength of calcium sulfate becomes. Due to the inherent properties of calcium sulfate, calcium sulfate powders need to be pre-treated in advance. The pre-treatment of calcium sulfate powders includes 1) classification; 2) blending; 3) mixing; 4) ball grinding and 5) granulating.

Laser particle diameter analysis and X-rays are used for granule comparison.

BRIEF DESCRIPTION OF THE DRAWINGS

The file of this Patent contains at least one Drawing Figure executed in color. Copies of the Patent with color Drawings will be provided by the Patent and Trademark Office upon request and payment of the necessary fee.

DETAILED DESCRIPTION OF THE EMBODIMENTS

Wherever possible in the following description, like reference numerals will refer to like elements and parts unless otherwise illustrated.

Referring to FIG. 1A through FIG. 10, (1) calcium sulfate hemihydrate powders are sieved through powder vibration sieve. Meshes 100, 120, 100, 325, 400, 500 under ASTM standards are vibration sieved for 48 hours at 10% of relative humidity and 5° C. of operation temperature to avoid any chemical reaction occurring when the powders contact with air. (2) The sieved calcium sulfate hemihydrate powders are subject to laser particle diameter analysis to select powders having particle diameter within certain range. (3) The selected powders are then subject to composition modification using oven with multiple heat treatment settings. Since calcium sulfate hemihydrate most of which are of α,β types tend to transform to calcium sulfate dihydrate as soon as contact with air, they must be stabilized individually. Modification time is about 48 hours and then the modified powders are taken out to store. (4) Powders with different particle sizes and composition are individually subject to X-ray confirmation. (5) Then, a tableting process is performed by adding 2% medication-level stearate coagulating agent.

2% of tablets, 500 g of tablets each batch, are arranged in matrix (10×10) at constant intervals in a steel stainless container. Total 5 batches are prepared. A powerful vacuum motor is used to evacuate air out of the container. Operation pressure is about 0-5 ATM. Pure water is poured at flow rate of 5 c.c./sec. Then the container is heated up to 100° C. at rate of 2° C./min. The relative humidity is in the range of 50-100%. Operation time is about 48 hours.

Figure 2A:
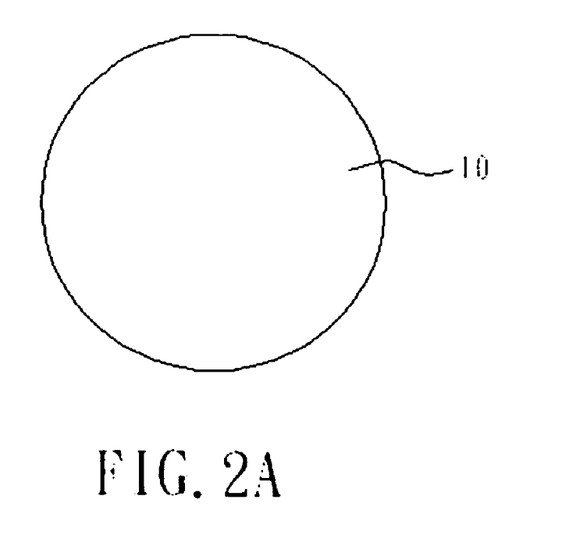
FIG. 2A illustrates the profile of a tablet before the humidification-vacuum process.
Figure 2B:
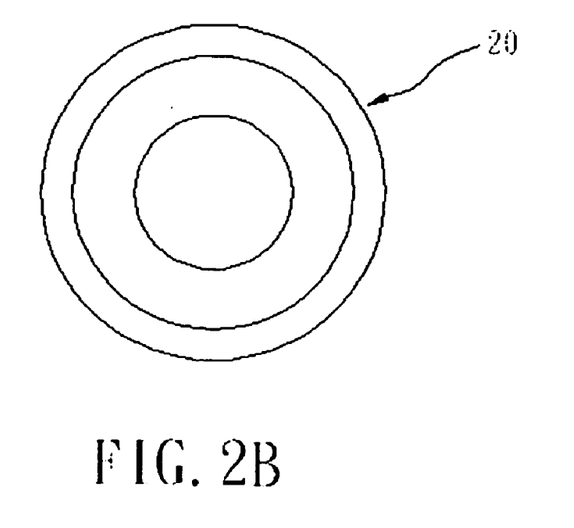
FIG. 2B illustrates schematic view of a tablet during or after the humidification-vacuum process.
Figure 2C:
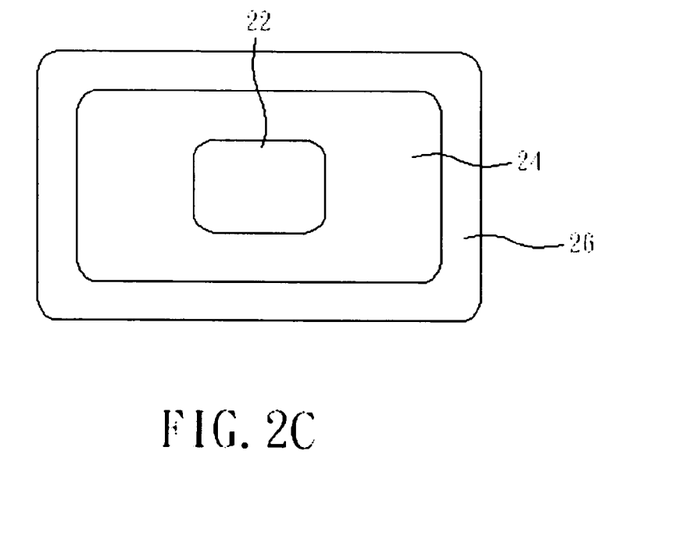
FIG. 2C illustrates schematic view of a tetragonal tablet during or after the humidification-vacuum process.

FIG. 2A through FIG. 2C are graphs showing the changes in structures of tablets in humidification-vacuum process. FIG. 2A illustrates the profile of granules 10 before the humidification-vacuum process. FIG. 2B illustrates a schematic view of granules 10 having a structure 20 of a laminate concentric circle during or after the humidification-vacuum process. FIG. 2C illustrates schematic view of a tablet having a tetragonal laminate structure including a calcium sulfate hemihydrate crystal layer 22, an interface 24 between calcium sulfate hemihydrate and calcium sulfate dihydrate and a calcium sulfate dihydrate crystal layer 26, during or after the humidification-vacuum process.

Figure 3A:
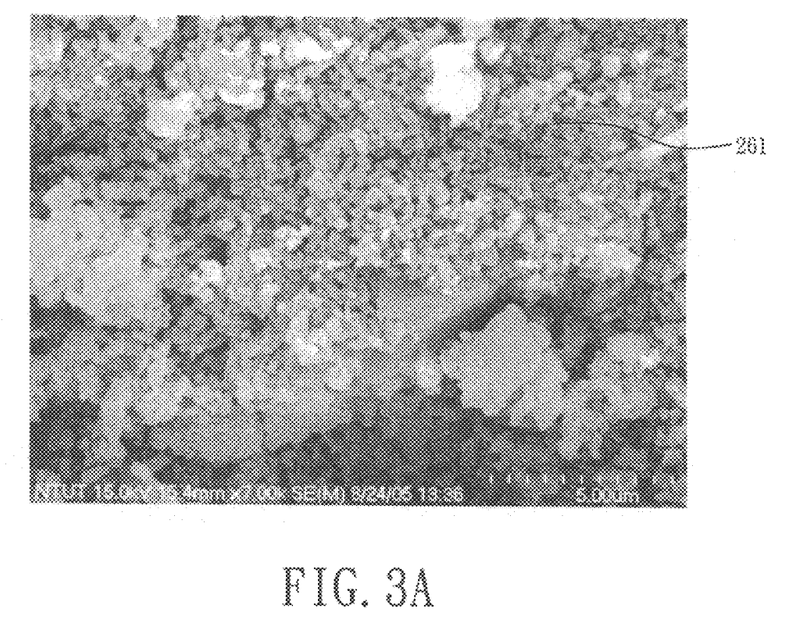
FIG. 3A is a microscopic view of outer configuration of a tablet which has a laminate concentric structure during humidification-vacuum process.
Figure 3B:
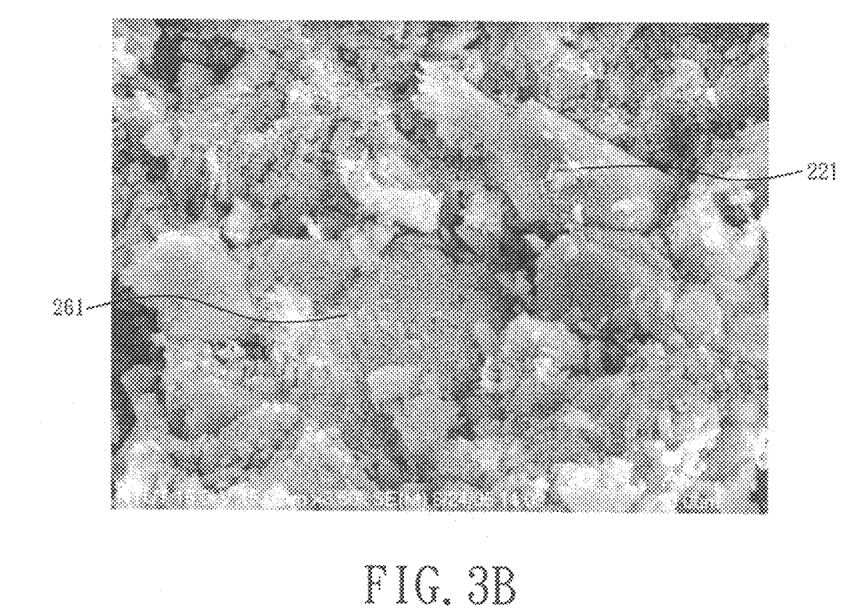
FIG. 3B is a microscopic view of an inner configuration of a tablet which has a laminate concentric structure during humidification-vacuum process.
Figure 3C:
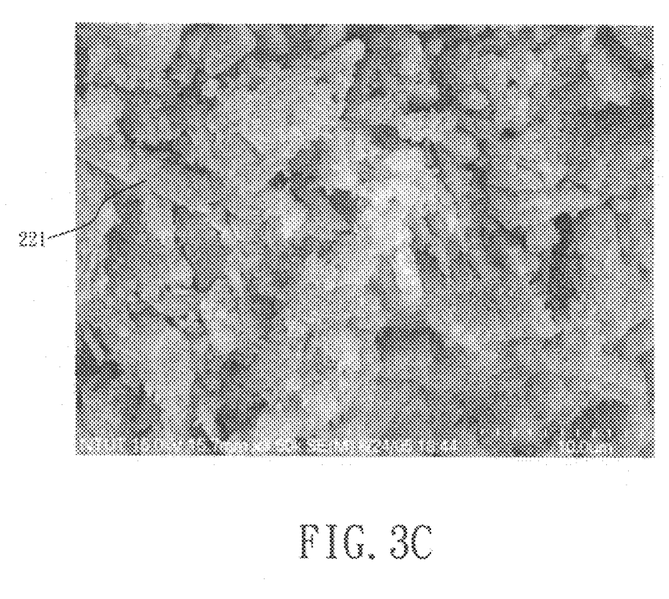
FIG. 3C is a microscopic view of a core configuration of a tablet which has a laminate concentric structure during humidification-vacuum process.

FIG. 3A through FIG. 3C are microscopic views of structures of tablets during humidification-vacuum process.

FIG. 3A is a microscopic view of outer configuration of a tablet which has a laminate concentric structure during humidification-vacuum process. In FIG. 3A, calcium sulfate dihydrate crystalline granules 261 are observed.

FIG. 3B is a microscopic view of an inner configuration of a tablet which has a laminate concentric structure during humidification-vacuum process. In FIG. 3B, calcium sulfate hemihydrate crystalline granules 221 and calcium sulfate dihydrate crystalline granules 261 are observed.

FIG. 3C is a microscopic view of a core configuration of a tablet which has a laminate concentric structure during humidification-vacuum process. In FIG. 3C, calcium sulfate hemihydrate crystalline granules 221 are observed.

Figure 6:
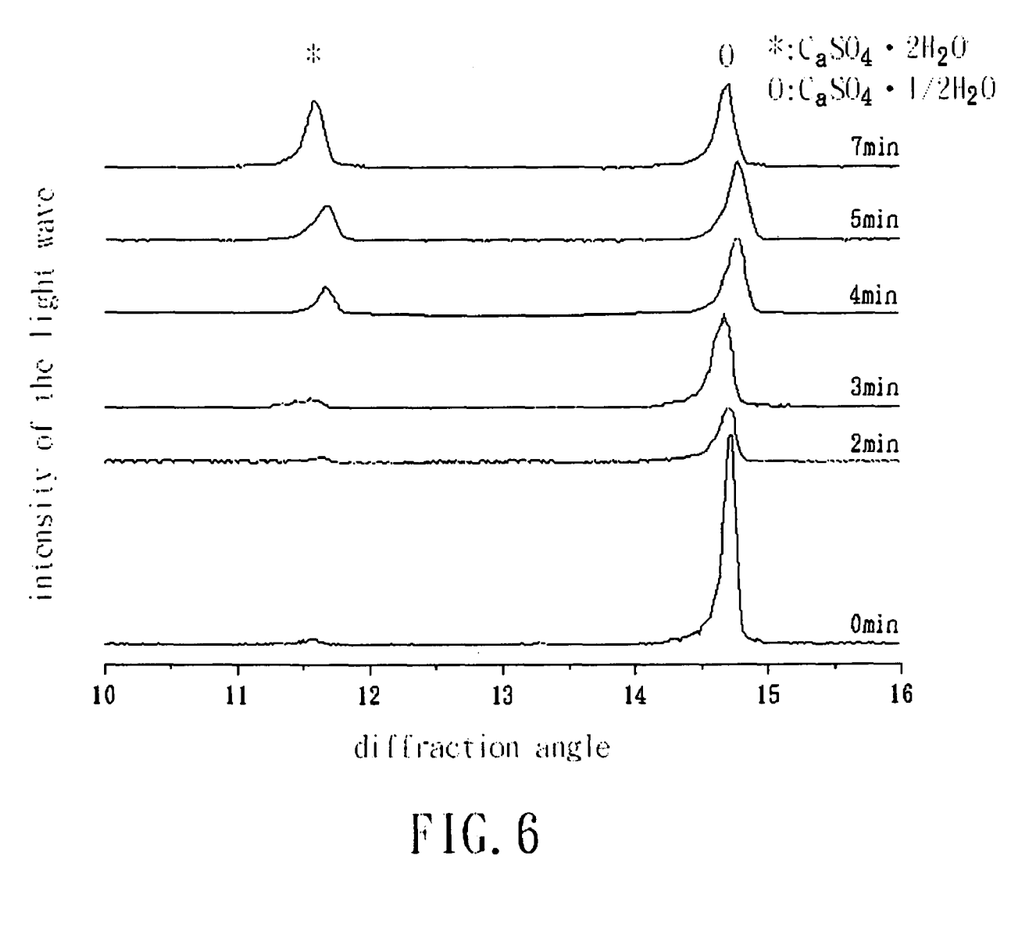
FIG. 6 is a graph of X-ray refraction on reactant versus time elapsed during humidification-vacuum process according one embodiment of the invention.

FIG. 6 illustrates graph of X-ray refraction on reactant versus time elapsed during humidification-vacuum process according to one embodiment of the invention. It is observed that the inventive process provides a pretty good yield.

Figure 7:
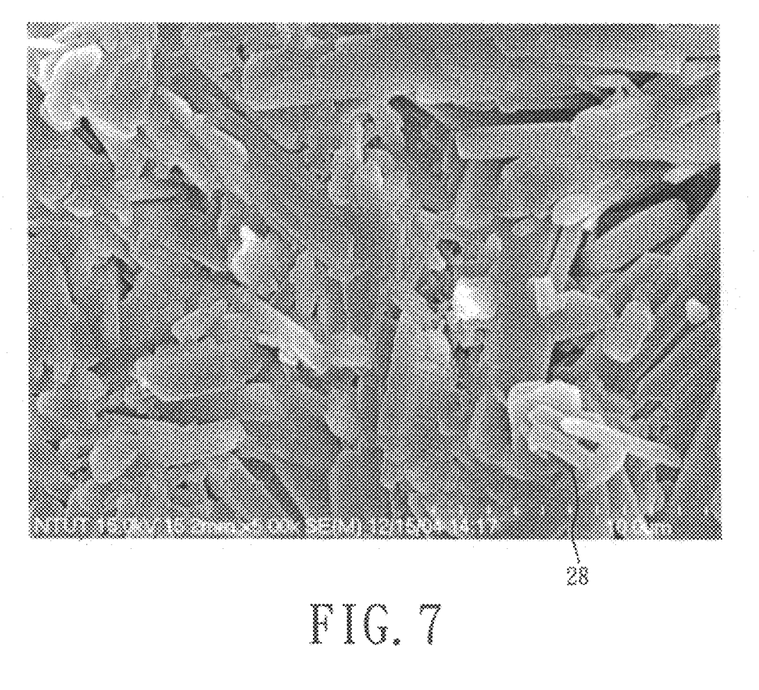
FIG. 7 is a microscopic view of an outer configuration of a tablet after humidification-vacuum process according to one embodiment of the invention.

FIG. 7 is a microscopic view of an outer configuration of a tablet which has a laminate concentric structure after humidification-vacuum process according to one embodiment of the invention. From FIG. 7, the inventive process and product achieve a good anti-dissolving performance, in which calcium sulfate anhydrate or dihydrate crystals 28 are at stable non-dissolvable status.

Figure 8:
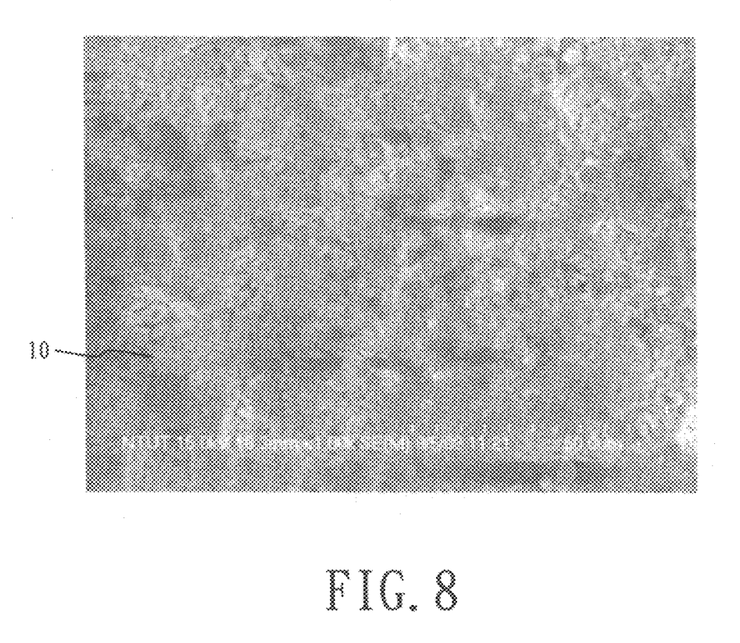
FIG. 8 is a microscopic view of an outer configuration of a granule before humidification-vacuum process according to one embodiment of the invention.

FIG. 8 is a microscopic view of an outer configuration of a granule before humidification-vacuum process according to one embodiment of the invention. In FIG. 8, hybrid but fewer crystals are observed on surfaces of the granules 10.

Figure 1A:
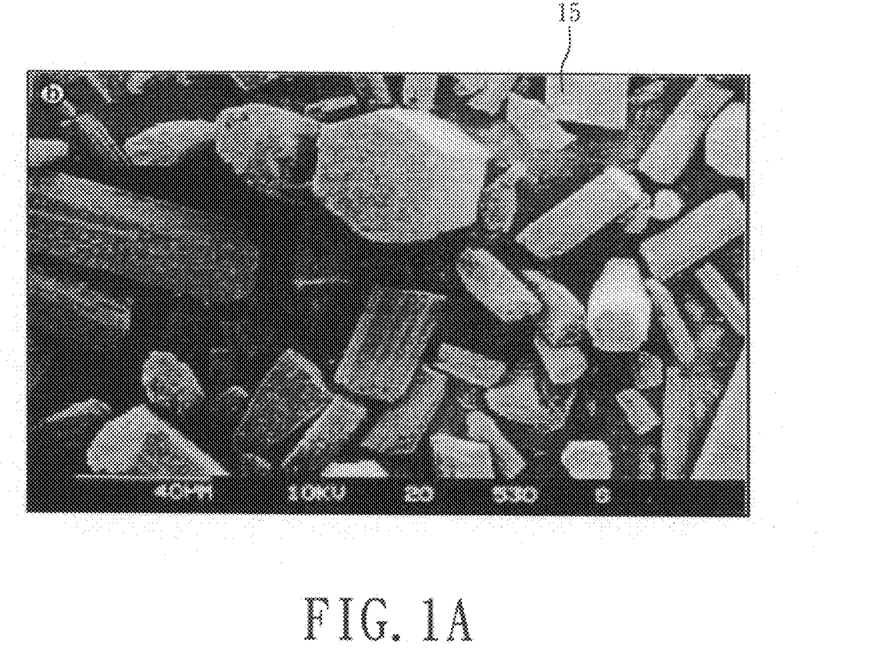
FIG. 1A is a microscopic photo of calcium sulfate anhydrate crystals formed by an ideal process.
Figure 1B:
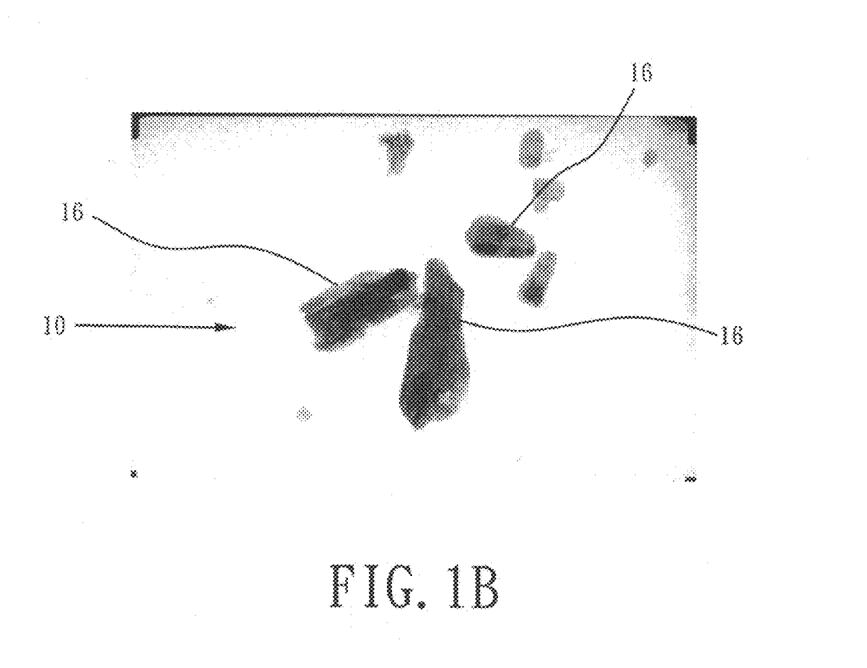
FIG. 1B which is a microscopic photo of calcium sulfate hemihydrate powders formed by a known industrial process.
Figure 1C:
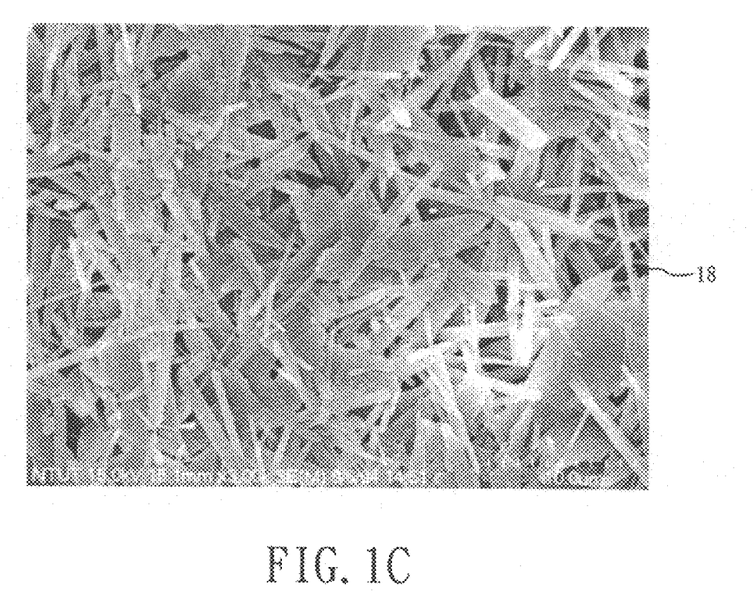
FIG. 1C which is a microscopic photo of calcium sulfate dihydrate powders formed by a known industrial process.
Figure 5A:
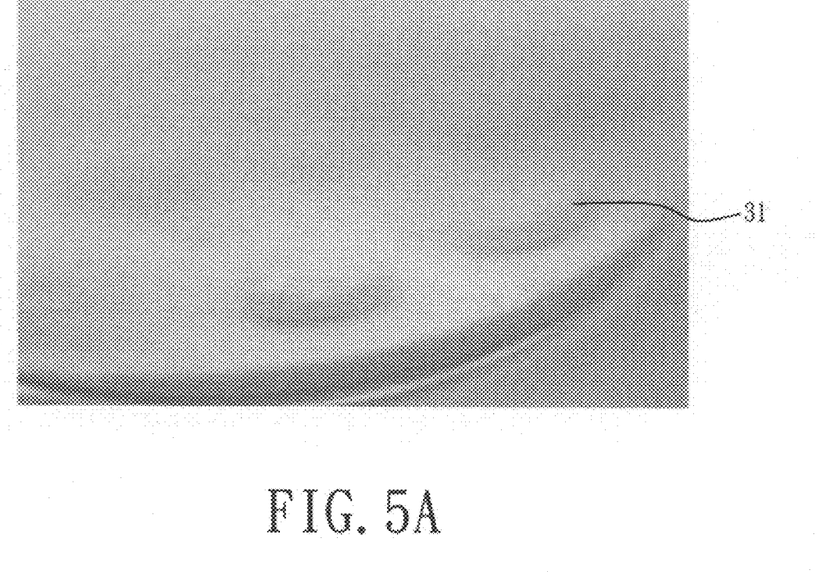
FIG. 5A illustrates the dissolving status of untreated calcium sulfate granules which have been subject to dissolution test for one week.
Figure 5B:
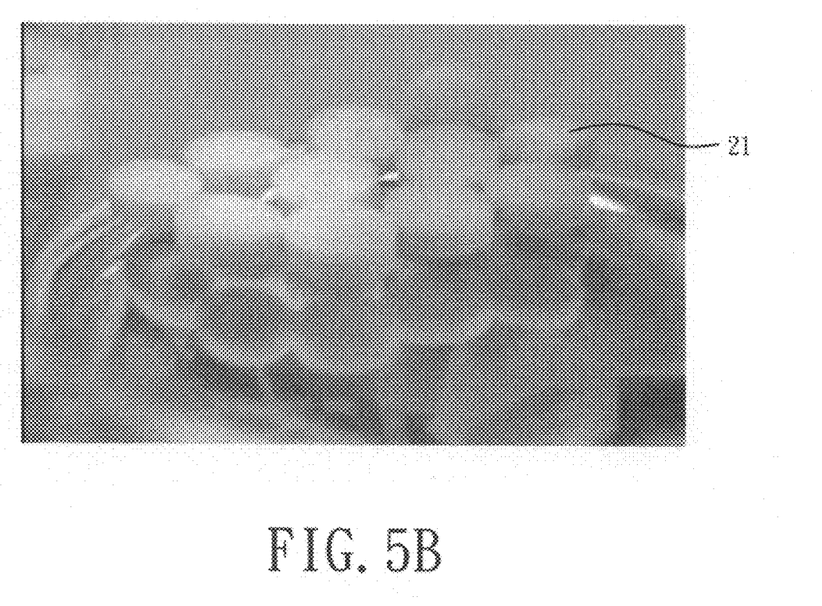
FIG. 5B illustrates the stable status of the inventive tablets which have been subject to dissolution test for one week.

Microscopic structures of reactants and stuffs used in the inventive process are shown as well. $CaSO_4$ (C.S. anhydrate) is shown in FIG. 1A which is a microscopic photo of calcium sulfate anhydrate crystals 15 formed by an ideal process). $CaSO_4 \cdot \frac{1}{2}H_2O$ (C.S. hemihydrate) is shown in FIG. 1B which is a microscopic photo of calcium sulfate hemihydrate powders, including granules and blocks 16 of calcium sulfate hemihydrate, formed by a known industrial process). $CaSO_4 \cdot 2H_2O$ (C.S. dihydrate) is shown in FIG. 1C which is a microscopic photo of calcium sulfate dihydrate crystals 18 formed by a known industrial process. The chemical equation is as follows:

Dehydration $CaSO_4 \cdot 2H_2O \rightarrow CaSO_4 \cdot \frac{1}{2}H_2O + \frac{3}{2}H_2O$ Hydration $CaSO_4 \cdot \frac{1}{2}H_2O + \frac{3}{2}H_2O \rightarrow CaSO_4 \cdot 2H_2O$ Furthermore, dissolution test in solution is performed for one week. FIG. 5A shows a blank sample not treated by the inventive process. FIG. 5B shows the tablets formed by the inventive process.

The thus-formed tablet is immersed in Hanks' solution. The result thereof indicates there no cracks occur, but there appear some spots of coagulating agent on surfaces of the tablet. Contrast to the tablet made by the inventive process, the blank sample cracks as soon as it immerses in the Hanks' solution.

Figure 9:
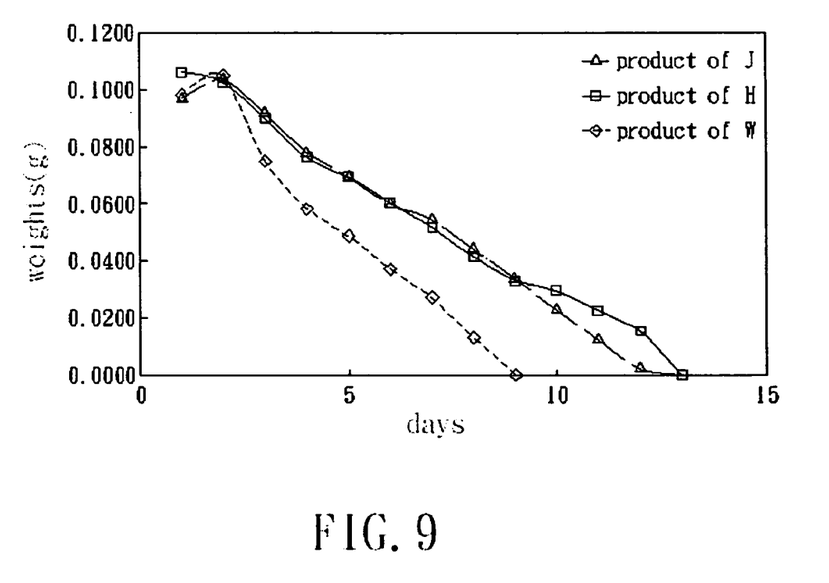
FIG. 9 illustrates results of dissolving rate tests on various products.

A dissolving rate test is performed in turn, as shown in FIG. 9.

(1) 100 g of tablet obtained by the process of the invention is weighted and still placed at relative humidity of 10%. After the tablet is weighted again, it is immersed in Hanks' solution of 1 L. Rinse the tablet per 24 hours. Put the tablet in oven at 70E1 for 4 hours and weight it again. Weight loss is calculated.

(2) The blank sample in this test is OSTEOSET (product of W-Wright) and JAX (product of J-Smith). Relative weight loss is got for dissolving rate analysis.

(3) Determine the dissolving rates using obtained weight loss.

One 14-week dissolution test, using pellet products of Wright and Smith (product J&H-Wright) as blanks is performed. It is noted that relative dissolving rates are analyzed due to difficulty of sampling. As shown from test data, it indicates that the tablets formed by the process of the invention, along with the blanks, remain dissolved at certain rates at the first and second weeks. At the third week, blank OSTEOSET (product of Wright) lost a lot of weight and totally disappears until the eighth week. Using certain tableting design and gel solution, JAX-series product disappears until thirteenth week.

The tablet treated by the inventive process has a lower dissolving rate, under longtime immersion.

Figure 4A:
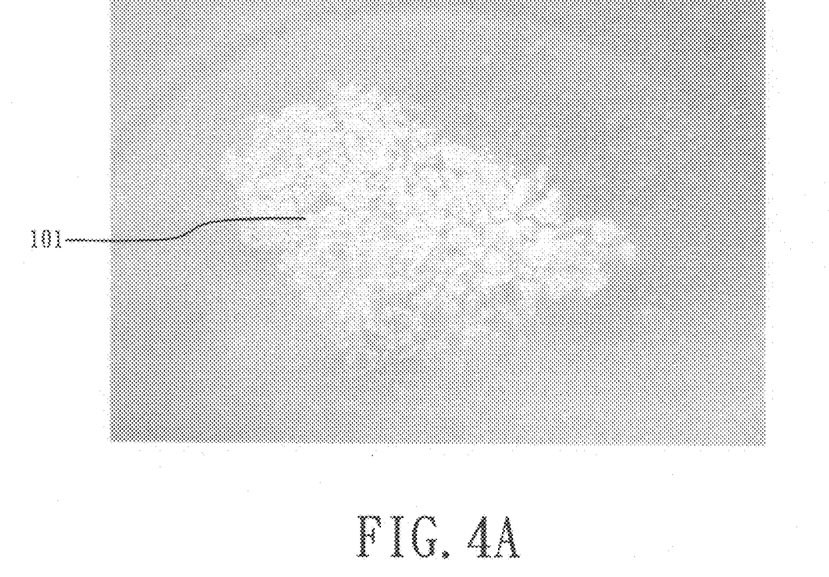
FIG. 4A shows appearance of powders before made into tablets according to one embodiment of the invention.
Figure 4B:
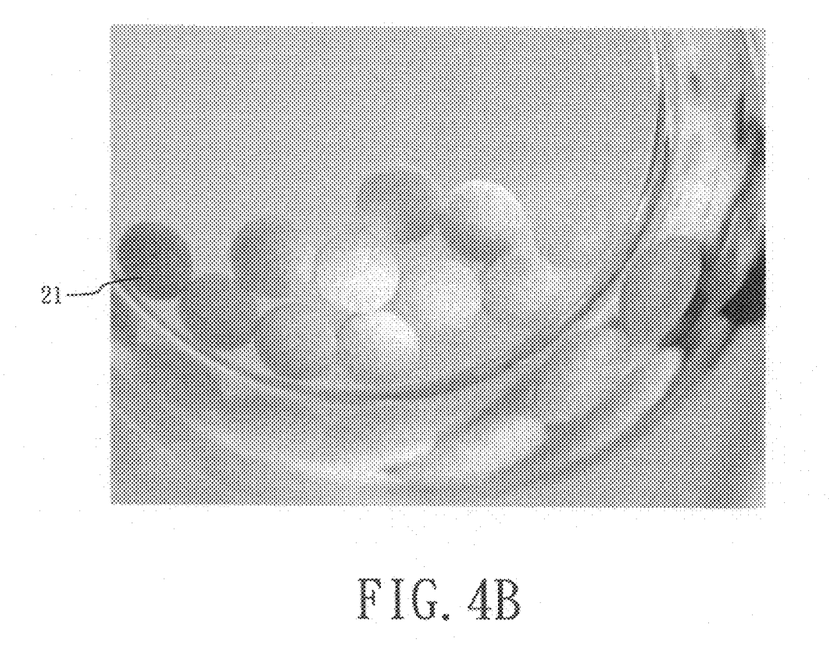
FIG. 4B shows appearance of treated tablets of calcium sulfate according to one embodiment of the invention.

It is clear to tell the change in appearances before and after the tablet is made from FIG. 4A and FIG. 4B which respectively show the appearances of powders 101 before made into tablets and of treated tablets of calcium sulfate 21. It is clear to tell the change in appearances before and after the tablet is made from FIG. 5A and FIG. 5B which respectively illustrate the dissolving status of untreated calcium sulfate granules 31 which have been subject to dissolution test for one week, and the stable status of the inventive tablets 21 which have been subject to dissolution test for one week.

In another embodiment, calcium phosphate salt is used and reacts with water to form hydroxyapatite $Ca_{10}(PO_4)_6(OH)_2$. The reaction scheme is as follows:

$10Ca_3(PO_4)_2 + 6H_2O = 3Ca_{10}(PO_4)_6(OH)_2 + 2H_3PO_4$ $Ca_2P_2O_7 + CaO + H_2O = Ca_{10}(PO_4)_6(OH)_2$ $10CaHPO_4 + 2H_2O = Ca_{10}(PO_4)_6(OH)_2 + 4H_3PO_4$

The process will be described in details. (1) Calcium phosphate powders are sieved through powder vibration sieve. Meshes 100, 120, 100, 325, 400, 500 under ASTM standards are vibration sieved for 48 hours. (2) The sieved calcium phosphate powders are subject to laser particle diameter analysis to pick up powders having particle diameter within certain range for purification. (3) The powders are then subject to composition modification using oven with multiple heat treatment settings. The modified powders are taken out after about 48 hours. (4) Powders of different particle sizes and composition are individually subject to X-ray confirmation. (5) Finally, tableting is performed by adding 2% medication-level stearate coagulating agent.

2% of tablets, 500 g of tablets each batch, are arranged in matrix (10×10) at constant intervals in a steel stainless container. Total 5 batches are prepared. A powerful vacuum motor is used to evacuate air out of the container. Operation pressure is about 0-5 ATM. Pure water is poured at flow rate of 5 c.c/sec. Then the container is heated up to 100° C. at rate of 2° C./min. The relative humidity is in the range of 50-100%. Operation time is about 48 hours.

Figure 10A:
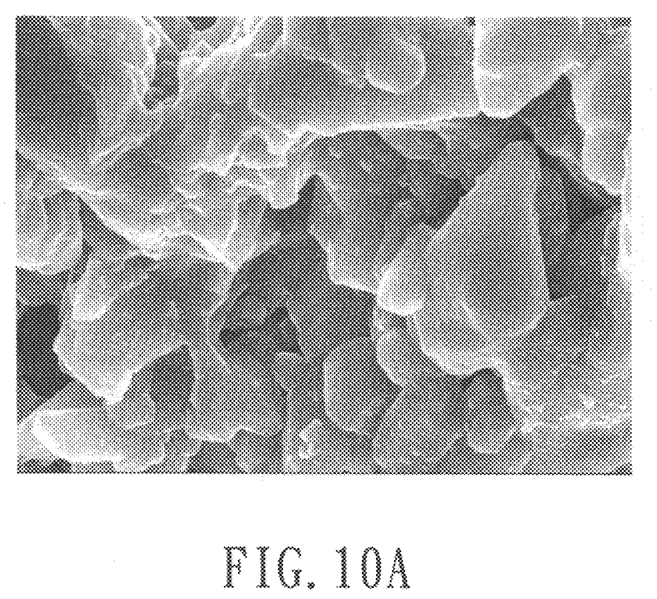
FIG. 10A is a microscopic photo showing the structure of the tablet before humidification-vacuum process according to one embodiment of the invention.
Figure 10B:
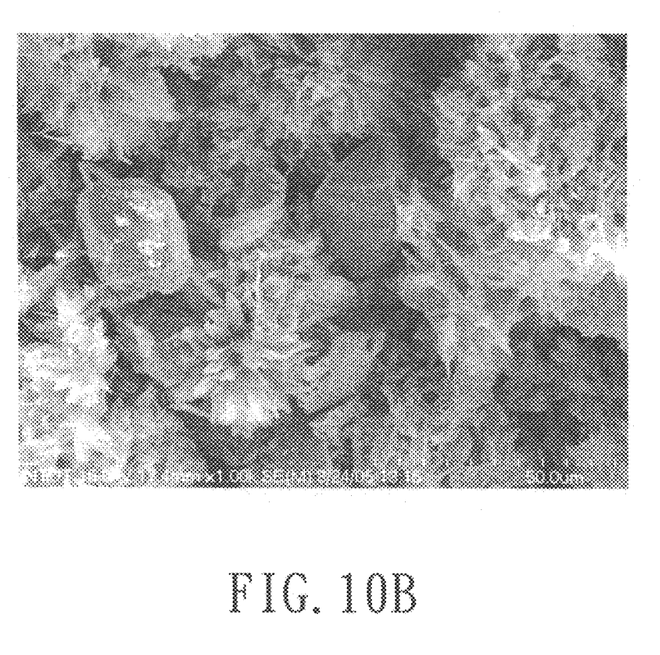
FIG. 10B is a microscopic photo showing the structure of the tablet after humidification-vacuum process according to one embodiment of the invention.

FIG. 10A is a microscopic photo showing the particle-shaped structure of the calcium phosphate tablet before humidification-vacuum process according to one embodiment of the invention;

FIG. 10B is a microscopic photo showing the flower-shaped structure of the tablet constituting by hydroxyapatite $Ca_{10}(PO_4)_6(OH)_2$ phase after humidification-vacuum process according to one embodiment of the invention.

In one embodiment of the invention, calcium sulfate powders need to be pre-treated in advance. The pre-treatment of calcium sulfate powders includes 1) classification; 2) blending; 3) mixing; 4) ball grinding and 5) granulating.

In another embodiment of the invention, the pre-treatment of powders includes 1) sieving; 2) purifying the structure of powders; 3) modifying and stabilizing; and 4) granulating.

The product of the invention is in the form of tablet. From microscope of view, it is of laminate calcium sulfate dihydrate crystals, homogeneous calcium sulfate dihydrate crystals or calcium phosphate crystals. Second phase of calcium sulfate dihydrate, whose structure is different from calcium sulfate hemihydrate crystals, is formed on surfaces of the tablet-shaped product. The laminate calcium sulfate dihydrate crystal has a structure of laminate concentric circle which helps control the dissolving rate. The tablet has dense crystal distribution. The tablet is in shape of circle, tetragon or triangle. Surfaces of the tablet can be used as one way for medicine release. 2% medication-level stearate is added in the tablet as coagulating agent.

Calcium sulfate salt and calcium phosphate salt that have been widely used, single or in mixture thereof, in orthopedics and dental departments are added additionally into the tablet. Liquid used in humidifying or wetting treatment can be saline solution, medication-level phosphoric acid and pure water. Conditions for humidification-vacuum process also include pressure of $10^{-1} \sim 10^{-6}$ torr. The structure of laminate concentric circle has various thicknesses depending on properties of treatment liquids. Void formed in the laminate structure can be the locations where different medicine can be doped for specific medical requirements.

The product of the invention is in the form of tablet for controlling the dissolving rate of bio-medical orthopedic implant material. From microscope of view, it is of laminate calcium sulfate dihydrate crystals, homogeneous calcium sulfate dihydrate crystals or calcium phosphate crystals. The second phase of calcium sulfate dihydrate, whose structure is different from calcium sulfate hemihydrate crystals, is formed on surfaces of the tablets. The laminate calcium sulfate dihydrate crystal has a structure of laminate concentric circle which helps control the dissolving rate of the tables. The tablet has dense crystal distribution.

Figure 11:
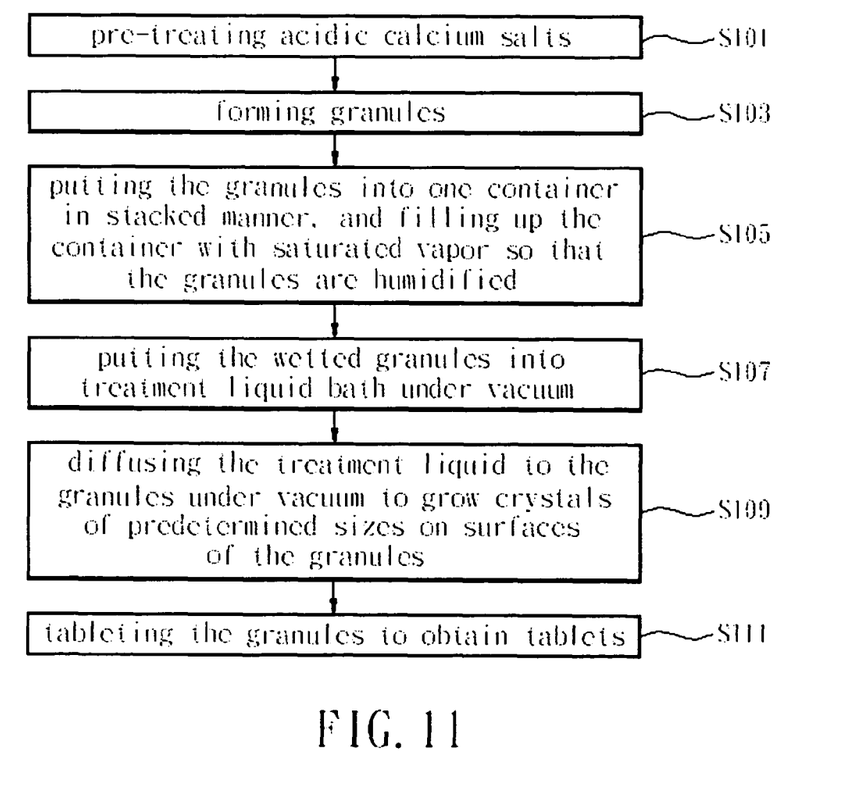
FIG. 11 is a flow chart of process of manufacturing products which can control dissolving rate of bio-medical orthopedic implant material according to one embodiment of the invention.

As shown in FIG. 11, the process of the invention includes pre-treating acidic calcium salts (step S101) to form granules (step S103); putting the granules into one container in stacked manner, and filling up the container with saturated vapor so that the granules are humidified (step S 105); putting the wetted granules into treatment liquid bath under vacuum (step S 107); diffusing the treatment liquid to the granules under vacuum to grow crystals of predetermined sizes on surfaces of the granules (step S 109); and tableting the granules to obtain tablets (step S111). In one embodiment of the invention, acidic calcium salt can be calcium sulfate salt or calcium phosphate salt, used single or in mixture thereof. In another embodiment of the invention, the acidic calcium salt can be calcium sulfate hemihydrate.

It is noted that the dissolving rate is controlled by controlling the crystallinity with kits that are not expensive or not commercially available. In addition, the product of the invention has calcium sulfate dihydrate which has structures of laminate concentric circles and complete crystals. The existing vacuum machine can be still used in the invention, which meets the need of practice use and efficient economy.

The invention provides some advantages, such as easy installation of new kits with low purchase cost and not high technology level, well controlled dissolving rate, and addition of auxiliary agents which is compatible with the whole process.

It should be apparent to those skilled in the art that the above description is only illustratives of specific embodiments and examples of the invention. The invention should therefore cover various modifications and variations made to the herein-described structure and operations of the invention, provided they fall within the scope of the invention as defined in the following appended claims.

The invention claimed is:

1. A process of manufacturing a product which can control dissolving rate of a biomedical orthopedic implant material, the process including:

Pre-treating of calcium sulfate salt powders to form granules;

Putting the granules into one container;

Wetting the container with vapor and then vacuuming the container to diffuse the vapor into the granules at a predetermined depth;

Crystallizing the granules to form an inner layer and an outer layer, the inner layer is a calcium sulfate hemihydrate crystal layer and the outer layer covering the inner layer is a calcium sulfate dihydrate crystal layer; and Tableting the granules to form tablets.

2. The process of claim 1, wherein the calcium sulfate salt is calcium sulfate hemihydrate.

3. The process of claim 1, wherein the granules are put in the container in a stacked arrangement.

4. The process of claim 1, wherein the calcium sulfate dehydrate crystal layer controls the dissolving rate of the tablets.

5. The process of claim 1, wherein the tablet is in flat or spherical shape of circle, tetragon or triangle, and the surfaces of tablets are used as ways for medicine release.

6. The process of claim 1, wherein 2% of medication-level stearate as a coagulating agent for tableting.

7. The process of claim 1, wherein at wetting step, the vapor is selected from the group consisting of saline solution, medication-level phosphoric acid, pure water or mixture thereof is used.

8. The process of claim 1, wherein the vacuum condition is $10^{-1} \sim 10^{-3}$ torr.

9. The process of claim 1, wherein the tablet has layered structure with voids formed therein, and the voids are the location where different medicine can be doped for different medical needs.

10. A process of manufacturing a product which can control dissolving rate of a biomedical orthopedic implant material, the process including:

Pre-treating of calcium phosphate salt powders to form granules;

Putting the granules into one container;

Wetting the container with vapor and then vacuuming the container to diffuse the vapor into the granules at a predetermined depth;

Crystal growing the granules to form an inner layer and an outer layer, the inner layer is calcium phosphate crystal layer, wherein the outer layer coving the inner layer is hydroxyapatite crystal layer; and Tableting the granules to form tablets.

11. The process of claim 10, wherein the granules are put in the container in a stacked arrangement.

12. The process of claim 10, wherein the hydroxyapatite crystal layer is used for control the dissolving rate of the tablets.

13. The process of claim 10, wherein the tablet is in flat or spherical shape of circle, tetragon or triangle, and the surfaces of tablets are used as ways for medicine release.

14. The process of claim 10, wherein 2% of medication-level stearate as a coagulating agent for tableting.

15. The process of claim 10, wherein at wetting step, the vapor is selected from the group consisting of medication-level phosphoric acid, pure water, or mixture thereof is used.

16. The process of claim 10, wherein the vacuum condition is $10^{-1} \sim 10^{-3}$ torr.

17. The process of claim 10, wherein the tablet has layered structure with voids formed therein, and the voids are the location where different medicine can be doped for different medical needs.

* * * * *